United States Patent [19]

Free et al.

[11] Patent Number: 5,187,079
[45] Date of Patent: Feb. 16, 1993

[54] GLUCOSE-REPRESSIBLE GENE FOR THE REGULATED EXPRESSION OF PROTEINS AND EXPRESSION VECTOR THEREFOR

[75] Inventors: Stephen J. Free, Williamsville, N.Y.; Mark T. McNally, Baltimore, Md.; Khaled A. Tarawneh, North Tonawanda, N.Y.

[73] Assignee: The Research Foundation of State University of New York, Albany, N.Y.

[21] Appl. No.: 288,687

[22] Filed: Dec. 21, 1988

[51] Int. Cl.$^5$ .................. C12P 21/00; C12N 1/15; C12N 5/10; C12N 15/80

[52] U.S. Cl. .................. 435/69.1; 135/254; 135/240.2; 135/320.1; 135/911; 536/23.4; 536/23.74; 536/24.1; 535/71; 535/68

[58] Field of Search .................. 935/41, 68; 536/27; 435/911, 320.1, 69.1, 71.2, 290.2, 252.3, 254

[56] References Cited

U.S. PATENT DOCUMENTS 4,661,454 4/1987 Botstein et al. .................. 435/256
4,727,028 2/1988 Santerre et al. .................. 435/240.2
4,894,333 1/1990 Cerretti et al. .................. 435/69.1

OTHER PUBLICATIONS

Henson et al. Transformation of Gaeumannomyecs-Graminis to Hemomyl Resistance, Curr. Genest. 14(2) 1988 113.
Pouwells et al. Cloning Vectors. Elsevier 1982.
Vollmer et al. 1986 E. efficient cloning of Genes of N. Crassa. PNAS83: 4869 McNally et al. 1988 Isolation & Characterization of a Neurosporaglucose repressible gene Curr. List 14:545.
Kinsey et al. 1984 Transformation of N. Crassa with the Cloned AM Gene, Mol. Cel. Biol. 4:117.

Primary Examiner—Richard A Schwartz
Assistant Examiner—John LeGuyader
Attorney, Agent, or Firm—Hodgson, Russ, Andrews, Woods & Goodyear

[57] ABSTRACT

A glucose-repressible gene comprising amino acid coding sequences of a desired protein and also an upstream regulatory region. An efficient expression vector comprising the regulatory region may be constructed to direct in a controlled manner, the production of recombinant products in N. crassa and related organisms.

13 Claims, 4 Drawing Sheets

Fig. 4A.

```
CAGCTGTAGA AGGAGCAGTC CATCTGCGTG AATCACGAGA GAATCAGCTA CTTTGAATCG   -867
ATGGATGCAC CCACATTATA TCCATGTCAC GGCTACGCGC CACATCACTG GGCACTTCAA   -807
TTGGGACAGG CATTGATCGG ACGAGACCGA CTTCTGGCCG CTTTCAACAG CCACATTATA   -747
TCCATGTCAC GGCTACGCGC GGCCTTCGGT AACAGAAAAG CACACAGACA GCGATTGTGA   -687
CATGGATTCG GGCAAACGAT TGGTGGTCGC ACCAGGTCAC CTGAGTGTGC AGTGGCTGCT   -627
ATTCAGATTT CATCTAACTG CGGGAGAGGG GTTCAAAGGG GCGTGACGTC ACAGACAACG   -567
GGTGAAGGAC G..AGATTGCC TCACTTCTTT GCTAGCAATT TGCCTGCAAA GAAGGCGCAC   -507
ATGACAAGCA AACAACTGGG AAACCACTAT TGAATACCCA CAATGCAAAG CTCGGAAGCT   -447
ACGTCTTGAT TGCAGTGTGT CGAGTGTCAA AAAAGAAGCA AGTGTTCATG CAAGCCAAAA   -387
TTGGCACCTC CTCCACTTCT CCGAGTGCCC CACCCGAACC TCCAGGCGAG ATGGCCGGAA   -327
CATACCATCC GCGTTGGGAT TATGACGTAT CTCCTTCTTC TTCACATGAT TCCATCCCGT   -267
TGTTGCTTGT TTGCGAGCTG TGACGGGAGA TCGTAGATGC CACTTCGGGC CAGGCAGGCA   -207
GTGCAGGCAG CCAGGAACAC AAGCTTCCAA CTTGGTCATC TCGATTGCCG ATTAAGGGAA   -147
                                                          ↓↓
CCAAATGCCT ATATAAGACT GTCCTCCCAC CTCCCCAATA CCATTCTTTT CTTCTTCCAT    -87
↓↓ ↓↓
CATCAGCCAA CAAAGCAATC ACATCTTCAC TACTTCAAAT CAACACAACA CTCAAACCAC    -27

TTTCACAACC CCTCACATCA ACCAAAATG GAT ACC CTC AAG AAC GCT GCC AAC      27
                               Met Asp Thr Leu Lys Asn Ala Ala Asn    9

TAC GTC GGT GAC AAC GTC CAG G gtaggtttcctcc agctctcgcc tccagcaccc    82
Tyr Val Gly Asp Lys Val Gln                                           16 gaggcacatc tcgggcatct tcacaacaac agacactgac atctcattct cacag GC     139
                                                               Gly    17

GCT ACC GCC ACT GCT TCC AAG GAG GCC AAC AAG GAC GTT GCC AAG GAC     187
Ala Thr Ala Thr Ala Ser Lys Glu Ala Asn Lys Asp Val Ala Lys Asp      33

TCC AAC CAG GGC GTC GGC ACT CG gtaagctcca tcacttttcc actctcacag     240
Ser Asn Gln Gly Val Gly Thr Arg                                      41 ccatcatcag acactaacat tcatcttcctctcag T CTC AAC GCT GCC GGT GAT     294
                                        Leu Asn Ala Ala Gly Asp      47

GCC ATC TCC GAC AAG GTC TCC GAG AAC AAG CAC GAC GCT AAG GCC GAG     342
Ala Ile Ser Asp Lys Val Ser Glu Asn Lys His Asp Ala Lys Ala Glu      63

GCC CAC AAG CAG GGT GCT ACC CAC TAA GCGACT TTACCAACAG TCGTTTTCCA    395
Ala His Lys Gln Gly Ala Thr His END                                  71

TTTCCTTTTT ATCAGTCATG ACTTGATGAT AATGGCCGGC TAAGGAGTTC GCCAAGGGCT   455
TCTCTATGAC ATACTTGGCT TGCAATTTCG AAGGGCAGCT TTAGCATTAC ACCAGAACCG   515
ATACCCCTAT TACATAGGCA TGGACACTGG TCCGTTCTAG CTAGGAATTG ACCCGGCTCT   575
             **
CTGCCAATTA ATACCTTCAC ATCTGTTTTT TTCCTCTTTG TTTTGTGAC ATTGACATTG   635
CCTTTCTGAC ATTGCTGTGT GCTTTGCAAC TTTGATCTTT ATAATTCTAC TTTGGCATTT   695
GGGGGGATTA TAAATGAGCC ATCGTCTTCA CGACTTGACT TAATGTAATA GCAGTGACAC   755
GAAAAGTTCG CCAAACATCA ACAACCCCAA ATGTCTTGCA TGAGAGAGTG TTGATCCAGA   815
CCCTCAATAA GCTGAACGAC ACTAGCAGGG GCTGTGCACG GCCCACAAAG ATCAGCCCTC   875
GCGATGAACT TCGCGTCCTT CAAGATTTCG GAGGCCACTT CGTTGAGGCC CAGCATCCTT   935
TCGTCAACTC GGCAAGAAAC ACAGCTG                                        962
```

Fig. 4B.

```
DNA Length: 1470
First nucleotide: +1
First nt.      10         20         30         40         50         60         70         80         90        100
                -          -          -          -          -          -          -          -          -          -
#1     CTCGAGTTGC ACGTGCCCTT TCTTGCACAC GAGTTCGCCT GTTAAAACAT CCCGGCGTCA AGGGCAGTCG CTGTCCGTTG GTCTACCCGT TCATTGGAAT
#101   TTCTCTTGGC GGCCTTGGTG AGGATGGCTC GATGGTTAT ACGGAGTTCG GTTGAACGTG GCACTGATGC GAGCTGCTTC TGTTACACCC GACGAAGTCG
#201   GTCTTCCTCC CAACATCCGT CCTGAACCTG CTTCACCCAC GAAACCGAGA TGATGCCACT GCACGATCTG ACCACCCTCC CAAATTCTGT TGAGTCTTGA
#301   CTCTCAACAA GTGCCCCGGC CTGTTGCCTT TCACCCACGT CAAGAATGCC AACGAGAGA ACGCCCTGTG CTCCTTCCAT CTCATAGATC GTGATATTTG
#401   ATTTTGCAAA CGGGTAAGAA CTTGACGGCA CCTGTCAGCT GATGAAGAAA AGGCAAGTTC CAACCGGGCG CAATCATCGC TAAGCTCAAG AAGCTAATGG
#501   TTCCTGCCGC TCATATCTGT TGATGGATAT TGGTACATCG ACCTCTGCAT GGTTAGCTTG GTACGATGAG CCTACATAAA
#601   ATATGGAGTA GACAGATGAC AGGAGAGCCA TTTCCTGTGC CAAAACCAAG ACTCGCAGGA CTTCTTTGCC ACCGAGCTAA TATTACACT ACACAATGCA
#701   GAGGCGCCCA AGCTGCAAGT CATCGCCGAT TCGTTTCATC TCGAGCCAGG CTCGCAGGCA CAAAGCACGC TGGGAAGAGG AGCAACGTTG AGTGGGCGGG
#801   CCTCGAACCG TCGGTAGTTC CTCTTGCCAA TGGGATTCGC TGCCCGTGTT TGGCGAGCTT GGTCTCTAGT GCAGCAAC CCCTCATTTG GGGAATCCAG
#901   CGAGCAATCT GTTGCACGTT GGGAAAGGCA GGAGCGCAAT CTTCCTATCA GCTGCTCACA CTCGTCAGTG CATCATCGAA GAGCCGAATT GCCATGGAGA
#1001  AACAGGATGG GAATCTGGCA ATCCGAGGAA TCTGCCACT GGCTCCAACA GATCATTCAA CCGAGGCAGG AGGATCTACC TGTTCAGTC AATGCGAGGC GCCTTTCGTA
#1101  CGTTCATTA CAAAATTGAA CCAAGATCAA GATACCGTG TTCTCGGTTT CTAGCAGTGC GATACTATGG AGCCCACGGC AGTAGCTGAA GCAAGTCGGC
#1201  CGCAGCGGCT CCTCCCCAGA TTTCAGATTG TAGTATGTAC CTAGCAGTGC GGGATAATGG CCCATGATAAGT GGGCATAAGT ACATCAATAG TGCGGGCTCA GCTAATGGA
#1301  ATCGTTCTTT GACGGCCAGC GTCACTGGCC GTCACTGGCC CCCATGATGC CTCTTTCCAT TTCCGGAAGT ACATCAATAG TTGTGTACTT TCGCCTAAAC
#1401  ACGAGATGTG ATTCTCAGGC AACGACGCGG AAGGAGAGAG CCCAAAGTCG GGCCGTCTT GTTCCAGCTG
```

GLUCOSE-REPRESSIBLE GENE FOR THE REGULATED EXPRESSION OF PROTEINS AND EXPRESSION VECTOR THEREFOR

This invention was made with Government support under contract number DCB 8316111 awarded by the National Science Foundation. The government may have certain rights in this invention.

BACKGROUND OF THE INVENTION

This invention relates to a glucose-repressible gene and more particularly to a regulatory region from that gene.

Glucose is the preferred source of carbon and energy for cellular growth. Glucose repression, is a well-known phenomenon in which the presence of glucose in the medium represses the expression of a number of genes (glucose-repressible genes). Glucose repression is an important regulatory system present in virtually all cells and is well defined in certain prokaryotic cells such as $E.$ $coli.$ A regulatory region from a glucose-repressible gene may also have wide application. The use of a regulatory region to confer high level expression upon a recombinant DNA sequence coding for a desired protein would allow efficient production of the protein.

In the filamentous fungi, a number of enzymatic activities are expressed (derepressed) whenever glucose is limiting. These glucose-repressible activities allow the fungi to utilize alternate carbon and energy sources. Therefore, for example, fungal cells containing a recombinant DNA molecule encoding a desired protein could be grown in a glucose medium and during the exponential growth phase the desired protein would not be produced. As the cells reach the end of the growth phase the glucose would be depleted and the desired protein would be synthesized at high levels. This type of system has the advantage of not producing the protein during the growth phase, when it's presence might be deleterious to the fungus. However, large amounts of the protein may be produced during the late phases of growth, when there is a large number of cells.

The use of filamentous fungi to synthesize protein products would have the advantage that fungal cells will proteolytically process (cleave with proteases) the protein in the same manner as human cells. The process of adding carbohydrates, a process common in human cells, occurs in a similar fashion within the filamentous fungi. In order to produce a protein having normal biological activity in eukaryotic organisms these two processes (the proteolytic processing of the protein and the addition of carbohydrates) must occur. The filamentous fungi are easy to cultivate and have been used in industrial applications. For these reasons, a filamentous fungi which can effectively be used for industrial production of proteins is desirable.

Unfortunately, to date no such regulatory region has been used in chimeric form to allow the accomplishment of the above objectives.

SUMMARY OF THE INVENTION

The present invention comprises a eukaryotically active, fungus compatible, chimeric gene having a first component which codes for an mRNA, and a second component upstream therefrom which comprises a DNA sequence for the regulated expression of said mRNA, said expression being regulated by glucose. The invention also comprises a plasmid comprising the chimeric gene and a microorganism comprising the plasmid.

BRIEF DESCRIPTION OF THE DRAWINGS

For a further understanding of the invention as well as its characterizing features, reference should now be made to the following detailed description thereof taken in conjunction with the accompanying drawings, wherein:

FIGS. 4A and 4B show the DNA sequences found in the grg-1 region of the Neurospora genome. FIG. 4A shows the DNA sequence of the PvuII fragment containing the grg-1 sequence which encodes the grg-1 protein (the region depicted in FIGS. 2 and 3). FIG. 4B shows the DNA sequence directly preceding the sequence shown in FIG. 4A. The last six nucleotides shown in FIG. 4B are shown as the first six nucleotides shown in FIG. 4A. The arrows in FIG. 4A indicate the 5' termini of the grg-1 mRNA. The asterisk shows the 3' end of the mRNA (the site of poly A addition). The lower case letters indicate sequences not found in the mRNA (intron sequences).

DETAILED DESCRIPTION OF THE INVENTION

Figure 1:
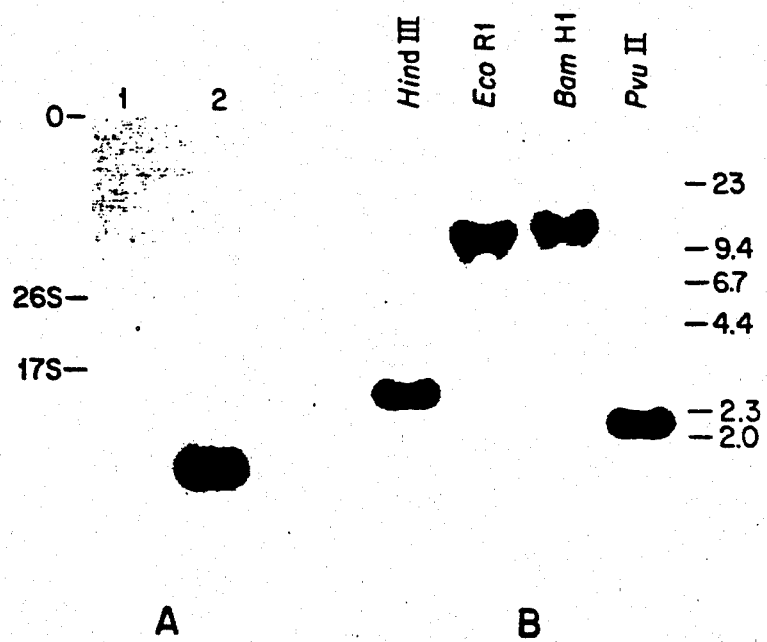
FIG. 1 section A shows an analysis of grg-1 mRNA levels as a function of extracellular glucose concentration. The section shows an autoradiograph of a Northern blot. Lane 1 contains RNA from a cell grown in glucose, lane 2 contains RNA from a cell which was transferred from a glucose medium to a glucose-free medium. Section B of FIG. 1 is an analysis of the $Neurospora$ $crassa$ genomic DNA. It shows a Southern blot of genomic DNA which has been digested with restriction endonucleases and hybridized with grg-1 sequences.

In accordance with this invention, a glucose-repressible gene, hereinafter identified as grg-1, is disclosed. grg-1 is a DNA which encodes a protein and also contains an upstream regulatory region. By regulatory region is meant a region containing DNA sequences needed for the efficient, regulated expression of grg-1 mRNA. The gene may be isolated and characterized from filamentous fungi. The grg-1 described herein has been isolated from the filamentous fungus $N.$ $crassa.$ This gene as found in $N.$ $crassa$ codes for a highly abundant mRNA which codes for a 7,000 molecular weight protein of unknown function. The regulatory region of grg-1 enables efficient expression of the mRNA. The regulatory region from this gene is used to construct an efficient expression vector to direct in a controlled manner, the production of recombinant products in $N.$ $crassa$ or related fungi i.e., Aspergillus species and other similar Ascomycetes.

The use of this regulatory region in a chimeric gene accomplishes essentially all of the goals previously described. Essentially, any DNA sequence may be inserted downstream from the glucose regulatory region.

Such sequences may be a DNA sequence coding for an mRNA for a desired protein such as insulin, interferon, and growth hormones. The sequence in a chimeric gene may be inserted into vectors such as the plasmids pSV50 or pBT3 and by means of such vectors enable in vivo production of a desired protein in various organisms such as *Neurospora crassa*. When such a plasmid is inserted into an organism such as *Neurospora crassa*, the plasmid sequences are often spliced into the cellular genetic material by the organism and expressed accordingly even though the independent plasmid may no longer exist. In either case, the glucose regulation may be retained.

The following examples and preparations describe the manner and process of making and using the invention and set forth the best mode contemplated by the inventor of carrying out the invention, but are not to be construed as limiting.

STRAINS AND GROWTH CONDITIONS/MATERIALS

Although most any Neurospora strain will suffice, the Neurospora strain 74-OR23-1a was the wild-type strain used for mRNA and DNA isolation in accordance with this description. This strain is available from Fungal Genetics Stock Center, Dept. of Microbiology University of Kansas Medical Center, Kansas City, Kans. 66103. Glucose-repressed cultures were grown in Vogel's N medium with 2% glucose for 18 hours at 30° C. Derepressed cultures were grown as above, then harvested on a Buchner funnel, washed with water, and resuspended in Vogel's salts with no carbon source for an additional 2 hours. *Escherichia coli* HB101, publicly available from Bethesda Research Labs, Gaithersburg, Md. 20877 and other sources known to those skilled in the art, were grown on L-broth with antibiotics and used for cloning and plasmid isolations. *E. coli* JM103, available from Pharmacia LKB, Piscataway, N.J. 08854 as well as other known sources, was grown on 2X YT-broth and used for the propagation of M13 phages.

Restriction enzymes, Klenow fragment, T4 DNA ligase, and T4 kinase were obtained from either Bethesda Research Labs or New England Biolabs. M13 rapid deletion constructs were produced with the Cyclone kit from International Biotechnologies, Inc. AMV reverse transcriptase was from Life Sciences, Inc. All enzymes were used according to the manufacturer's instructions. pGEM plasmids were the product of Promega Biotech. $^{32}$P-containing nucleotides were obtained from ICN Pharmaceuticals, Inc., Irvine, Calif.

All other microorganisms, plasmids or materials discussed herein are publicly available and may be obtained from various sources, well known to those skilled in the art. These sources include but are not limited to Bethesda Research Labs, Gaithersburg, Md.; New England Biolabs, Beverly, Mass.; Promega Biotech, Madison, Wis.; and Sigma Chemical Company, St. Louis, Mo.

ISOLATION OF grg-1

*N. crassa* DNA was isolated by the procedure of R. L. Metzenberg and T. J. Baisch (1981, "An Easy Method for Preparing *Neurospora* DNA," *Neurospora Newsl.* 28:20-21). *N. crassa* RNA was isolated by grinding mycelia to a fine powder under liquid nitrogen and processing this according to Chirgwin et al. (J. M. Chirgwin, A. E. Przybyla, R. J. MacDonald, and W. J. Rutter, 1979, "Isolation of Biologically Active Ribonucleic Acid From Sources Enriched in Ribonuclease," *Biochemistry* 18:5294-5299). Poly (A)+RNA was isolated from total RNA by oligo(dT)-cellulose chromatography. Plasmid DNA was isolated by the alkaline lysis method of B. C. Birnboim and J. Doly (1979, "A Rapid Alkaline Extraction Procedure for Screening Recombinant Plasmid DNA," *Nucleic Acids Res.* 7:1513-1523).

To isolate glucose-repressible genes from *N. crassa* a cDNA library was prepared from mRNA present in glucose-starved (derepressed) cells. To prepare the cDNA library, cDNA to derepressed mRNA was synthesized using minor modifications of the RNase H method described by O. Gubler and B. J. Hoffman (1983, "A Simple and Very Efficient Method for Generating cDNA Libraries," *Gene* 263-269). Double-stranded cDNA was tailed with deoxycytidine and annealed to pBR322 that had been cut with PstI and tailed with deoxyguanosine. This material was used to transform *E. coli* HB101 to tetracycline resistance.

To isolate grg-1 cDNA, cDNA copies of mRNAs expressed in derepressed but not repressed cultures of Neurospora were obtained by a differential screening of the above cDNA library. *E. coli* cells harboring cDNA clones were grown on duplicate nitrocellulose filters and screened by the method of M. Grunstein and D. Hogness (1975, "Colony Hybridization: A Method For The Isolation of Cloned DNAs That Contain A Specific Gene," *Proc. Nat. Acad. Sci. USA* 72:3961-3965) with radioactive single-stranded cDNA probes from derepressed and repressed mRNA. Several members of the library gave intense signals with the derepressed probe but little or no signal with the repressed probe. Northern blots of poly(A)+RNA from derepressed and repressed Neurospora cultures were probed with radioactively labeled cDNAs. The grg-1 cDNA hybridized strongly to a 680 nucleotide message present in derepressed, but not repressed, mRNA. Five independent cDNA isolates of grg-1 were obtained, the longest, p2D30, being 600 base pairs (bp).

These results can be seen in section A of FIG. 1 where 2μg poly (A)+mRNA from cells grown in glucose medium (lane 1) or transferred to carbon-free medium (lane 2) was separated by electrophoresis in a formaldehyde agarose gel, transferred to nitrocellulose, and probed with $^{32}$P-labeled p2D30. The hybridizing transcript is approximately 680 nucleotides. 26S and 17S refer to Neurospora ribosomal RNAs.

Hybridization of the cDNAs to Southern blots of Neurospora genomic DNA that had been cut with various restriction enzymes produced the same pattern. In section B of FIG. 1, genomic DNA digested with the indicated restriction endonucleases was subjected to Southern blotting and probed with p2D30. The sizes of the hybridizing DNA fragments were assessed by using HindIII fragments of lambda DNA as size standards. Results identical to sections A and B of FIG. 1 were obtained with all five grg-1 cDNA probes. It may be concluded that the five cDNAs must have arisen by synthesis from the same mRNA species.

As discussed above, Southern, and Northern blots were performed essentially as described by Maniatis et al. (R. Maniatis, E. F. Frisch and J. Sambrook, 1982, "Molecular Cloning: A Laboratory Manual," Cold Spring Harbor Laboratory, Cold Spring Harbor, N.Y.). Baked filters were prehybridized in bags in a solution of 6xSSC (1x is 0.15 M NaCl, 0.015 M sodium citrate), 5x Denhardt solution, 0.5% SDS, and 100 μg/ml denatured salmon sperm DNA. After approximately 4 h at 65° C., $^{32}$P-labeled probes were added and incubated at 60°-65° C. overnight. After hybridization, filters were washed in 2xSSC, 0.1% SDS at room temperatures for 1 h with four changes of solution, then in 0.2xSSC, 0.1% SDS at 65° C. for 1 h with four changes. Autoradiography of filters was performed with intensifying screens and x-ray film at −70° C. Suitable x-ray film include Kodak ® XAR-5, commercially available from The Kodak Company.

A genomic fragment containing grg-1 was isolated by screening a cosmid library of Neurospora DNA with nick-translated p2D30. A single member of the cosmid library was found which hybridized with the probe. Restriction analysis of the cosmid DNA indicated that a 1.9 kb PvuII fragment present in the cosmid hybridized with p2D30.

Figure 2:
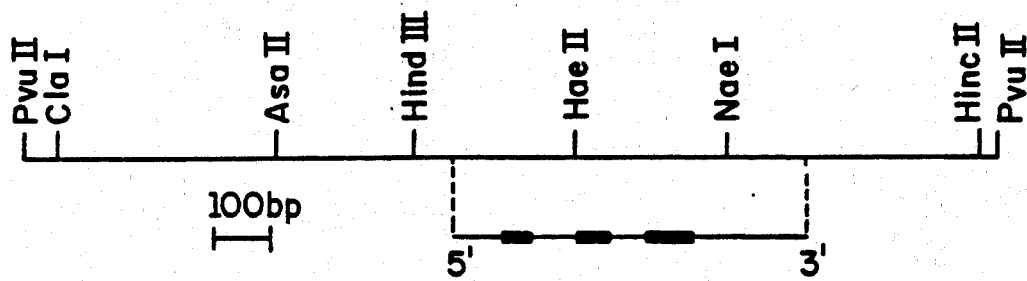
FIG. 2 shows a restriction map of the 1.9 kb $N.$ $crassa$ PvuII genome fragment which contains the region of grg-1 found in the grg-1 mRNA.

The cosmid DNA contained at least 12 kb in and around grg-1 (data not shown). The 1.9 kb PvuII cosmid fragment that hybridized with p2D30 was gel purified and cloned into the plasmid vector pUC9, generating a plasmid pGRG-1. pGRG-1 contains the amino acid coding region of grg-1. A restriction map was generated and is shown as FIG. 2. The locations of the restriction sites have been confirmed by DNA sequencing.

CHARACTERIZATION OF THE grg-1 GENOMIC CLONE

To further Characterize grg-1 the DNA sequence of the longest cDNA clone, p2D30, and genomic clones pGRG-1, and the region shown in FIG. 4B were obtained.

DNA sequencing was performed by the dideoxynucleotide chain termination method using M13 templates as described by Williams et al. (S. A. Williams, B. E. Slatko, L. S. Moran, and S. M. Desimone, 1986, "Sequencing in the Fast Lane: A Rapid Protocol for [a$^{35}$S]-dATP Dideoxy DNA Sequencing," Biotechnicues, 4:138-147). In addition, some double-stranded sequencing was done in pBR322, pUC9, and pGEM plasmids. Many of the M13 templates were obtained by the rapid deletion method of Dale et al. (R. M. K. Dale, B. A. McClure, and J. P. Houchins, 1985, "A Rapid Single-Stranded Cloning Strategy for Producing a Sequential Series of Overlapping Clones for Use in DNA Sequencing: Application to Sequencing the Corn Mitochondrial 18S rDNA," Plasmid 13:31-40).

Figure 3:
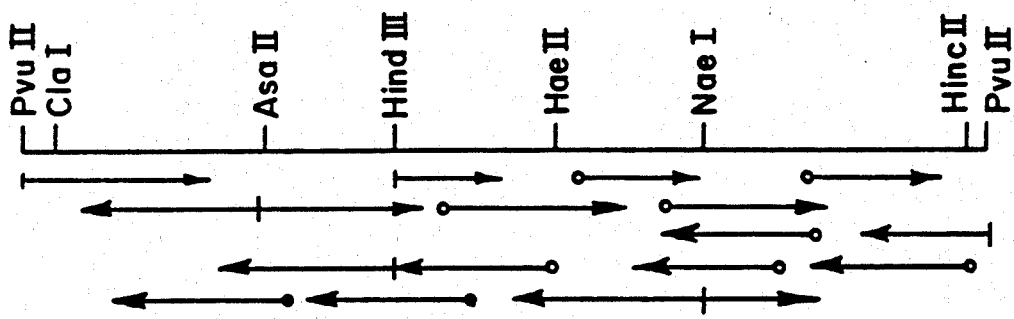
FIG. 3 shows the DNA sequencing strategy used to obtain DNA sequences from the PvuII fragment shown in FIG. 2.

The sequencing strategy for pGRG-1 can be seen from FIG. 3. Extent and direction of sequencing is indicated by the arrows. Arrows with open circles represent templates generated by the rapid deletion method of Dale et al, whereas those with solid circles were reactions using custom oligonucleotides. The resulting sequence is seen on FIG. 4A. Nucleotide numbering uses the initiation ATG as +1 and is located next to the nucleotide sequence. Lower case letters are used for intron sequences. Numbering of the deduced amino acid sequence is also shown beginning with the initiation methionine. Transcription start sites, as determined by primer extension, are denoted by arrows above the line. Asterisks indicate the 3' end of the mRNA. Solid lines above and below the intron regions show 5' and 3' splice-site consensus sequences, respectively. The longest cDNA contained a poly(A) region and 500 bp of sequence upstream from the poly(A) addition site (data not shown). Comparison of the cDNA and genomic sequences showed them to be identical except for two short introns present in the genomic clone. The 5' ends of these two introns begin with the sequence GTAGGT and GTAAGC (FIG. 4A). Each of these sequences contain only one base which differs from the 5' intron consensus sequence, GTA(A/C)GT, found for other Neurospora genes. Neurospora introns also contain a consensus sequence of (A/G)CT(A/G)AC(A/T) . . . 7 to 18 nucleotides . . . CAG at their 3' boundary. The two grg-1 introns end with ACTGACA . . . 11 nucleotides . . . CAG, and ACTAACA . . . 13 nucleotides . . . CAG, which are both perfect matches with the consensus sequence. No other intron consensus sequences in grg-1 genomic DNA were found.

The location of the 3' end of the mRNA transcript was determined by sequencing a cDNA construct. Poly(A) was found immediately after the C designated by the asterisk in FIG. 4A. It may be concluded that Poly(A) addition occurs after either this C or the following A.

The 5' end of the grg-1 transcript was mapped by primer extension experiments. In order to carry out the experiments, the oligonucleotide primer, 5'-CAATTTTGGTTGATGTGAGGGGTTGTGA-3', a sequence which is complimentary to a region near the 5' end of the longest cDNA, p2D30, was synthesized (Applied Biosystems DNA Synthesizer), 5' end labeled, and annealed to 30 μg total RNA (85° C. for 5 min; 65° C. for 120 min) in 30 μl of 240 mM KCl, 10 mM Tris-HCl (pH 8.0). The extension was carried out with AMV reverse transcriptase at 42° C. and 50° C. as described by Reeder et al. (R. H. Reeder, J. G. Roan, and M. Dunaway, 1983, "Spacer Regulation of Xenopus Ribosomal Gene Transcription: Competition in Oocytes," Cell 35:449-456).

Figure 5:
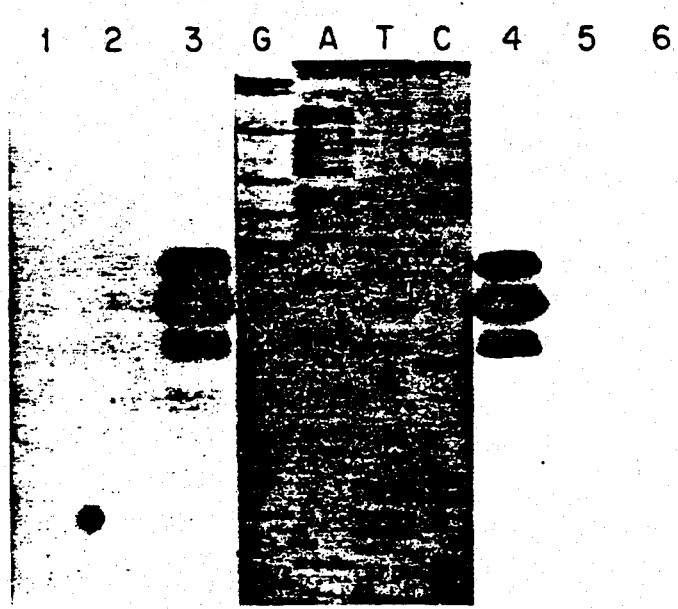
FIG. 5 shows a primer extension experiment which was used to determine the sequence at the 5' end of the mRNA.

As can be seen from FIG. 5, the oligonuoleotide primer, 5'-CAATTTTGGTTGATGTGAGGGGTT-GTAG-3', was able to hybridize to RNA from derepressed cells (lanes 3 and 4) and to be extended with reverse transcriptase. The extension products at 42° C. (lanes 3) and 50° C. (lanes 4) were subjected to electrophoresis in a sequencing gel along with double-stranded sequencing reactions of pGRG-1 produced with the same primer (lanes GATC). That these products are specific to extensions with derepressed but not repressed mRNA, and appear when reactions are done at both 42° and 50° C., suggests that the observed extension products represent distinct 5' termini. The positions of the termini are shown in FIG. 4A.

The region upstream of the PvuII fragment was cloned into pUC9 and M13 vectors. This region was sequenced in a manner similar to that used to sequence the PvuII fragment. The DNA sequence upstream of the PvuII fragment can be seen in FIG. 4B.

In accordance with the above procedures, the genomic grg-1 has been isolated and characterized. A region of 3,352 nucleotides has been sequenced. This region encompasses the mRNA coding region as well as 2,302 base pairs of 5' and 369 base pairs of 3' flanking sequence. grg-1 message levels were found to increase within minutes following the onset of glucose deprivation and rise 50-fold during the first 90 minutes of derepression.

REGULATION OF grg-1

The kinetics of grg-1 mRNA accumulation were examined by Northern blot analysis of RNA from cells that had been grown in a glucose medium (Vogel's N medium with 2% glucose) and transferred to a carbon-free medium (Vogel's N medium without glucose) for various lengths of time. Such a transfer is known to cause a rapid production of several glucose-repressible activities. A glucose-repressed culture of *N. crassa* was transferred to derepression media, aliquots withdrawn at various times, and total RNA isolated. A Northern blot was prepared and hybridized with nick-translated p2D30. The level of grg-1 mRNA was found to increase within 5 minutes of derepression and to rise dramatically during the first hour in glucose-free medium.

grg-1 DERIVED EXPRESSION VECTORS

The grg-1 regulatory region can be used to construct an efficient expression vector to direct the production of a protein in *N. crassa* or a related organism. The production of the protein would be regulated by the availability of extracellular glucose. Thus, during a fermentation in the presence of glucose, the protein of interest would not be synthesized during the exponential growth phase but its synthesis would be automatically turned on and the protein would be produced at high levels as the cells approach the stationary phase of growth.

Virtually any protein may be expressed using the present invention. Examples of possible desirable proteins include but are not limited to human growth hormone, insulin and interferon.

An example of how the grg-1 regulatory sequences could be used for the production of a desired protein is given below.

Using standard techniques known by those skilled in the art, (Maniatis et al., supra), the region between the grg-1 initiation of translation site and the termination of translation site (nucleotides #1 and #369 in FIG. 4A) would be replaced by the amino acid coding sequences of the desired protein to create a chimeric gene. For example, the amino acid coding sequence for insulin may be used.

The chimeric gene would then be placed into a plasmid vector whose presence can be selected for in fungal transformants. Vectors which may be selected for in fungal transformants are those which have a selectable gene (a gene which allows the presence of the plasmid containing the chimeric gene to be detected). Examples of selectable genes are as follows: am (glutamate dehydrogenase-ammonium metabolism); pyr 4 (pyrimidine biosynthesis); trp 1 (tryptophan biosynthesis); his 3 (histidine biosynthesis); benomyl or other antibiotic resistance gene.

Examples of suitable vectors are pSV50 and pBT3 which contain the selectable benomyl resistance gene. The chimeric gene may be inserted into the above vectors utilizing procedures known in the art as discussed by S. J. Vollmer and C. Yanofsky (1986, "Efficient Cloning of the Genes of *Neurospora crassa*," *Proc. Natl. Acad. Sci. USA* 83:4869–4873); and M. J. Orbach, E. B. Porro, and C. Yanofsky (1986, "Cloning and Characterization of the Gene for β-tubulin from a Benomyl-resistant Mutant of *Neurospora crassa* and its Use as a Dominant Selectable Marker," *Mol. Cell. Biol.* 6:2452–2461).

The plasmid vector containing the chimeric gene would then be used to transform Neurospora cells. A cell containing the above constructed plasmid sequences would be isolated. The cell would be placed in a glucose-containing medium within a fermentation vessel and allowed to rapidly grow and divide. As the culture uses up the glucose (late log phase) the grg-1 regulatory region will turn on the production of the mRNA encoding the desired protein and large amounts of the desired protein would be synthesized. The culture would be harvested and the protein would be purified.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

What is claimed is:

1. A eukaryotically active, fungus compatible chimeric gene comprising:
   a) a glucose-repressible gene region, wherein said region consists essentially of the following nucleotide sequence:

```
CAGCTGTACA AGGAGCAGTC CATCTGCGTG AATCACGAGA GAATCAGCTA
         -867
CTTTGAATCG  ATGGATGCAG CTACCAGAAG TCACTCAGTT CGTTCAAAGC
                      -807
CACATCACTG GGCACTTCAA  TTGGGACAGG CATTGATCGG ACGAGACCGA
                              -747
CTTCTGGCCG CTTTCAACAG CCACATTATA  TCCATGTCAC GGCTACGCGC
                                        -687
GGCCTTCGGT AACAGAAAAG CACACAGACA GCGATTGTGA  CATGGATTCG
                                                -627
GGCAAACGAT TGGTGGTCGC ACCAGGTCAC CTGAGTGTGC AGTGGCTGCT

ATTCAGATTT CATCTAACTG CGGGAGAGGG GTTCAAAGGG GCGTGACGTC
         -567
ACAGACAACG  GGTGAAGGAC GAAGATTGCC TCACTTCTTT GCTAGCAATT
                     -507
TGCCTGCAAA GAAGGCGCAC  ATGTCAAGCA AACAACTGGG AAACCACTAT
                              -447
TGAATACCCA CAATGCAAAG CTCGGAAGGT  ACGTCTTGAT TGCAGTGTGT
                                       -387
CGAGTGTCAA AAAGAAGCA AGTGTTCATG CAAGCCAAAA  TTGGCACCTC
                                                -327
CTCCACTTCT CCGAGTGCCC CACCCGAACC TCCAGGCGAG ATGGCCGGAA

CATACCATCC GCGTTGGGAT TATGACGTAT CTCCTTCTTC TTCACATGAT
        -267
TCCATCCCGT  TGTTGCTTGT TTGCGAGCTG TGACGGGAGA TCGTAGATGC
                    -207
CACTTAGGGC CAGGCAGGCA  GTGCAGGCAG CCAGGAACAC AAGCTTCCAA
                              -147
CTTGGTCATC TCGATTGCCG ATTAAGGGAA  CCAAATGCCT ATATAAGACT
                                         -87
GTCCTCCCAC CTCCCCAATA CCATTCTTTT CTTCTTCCAT  CATCAGCCAA
                                                -27
CAAAGCAATC ACATCTTCAC TACTTCAAAT CAACACAACA CTCAAACCAC

TTTCACAACC CCTCACATCA ACCAAAATG GAT ACC CTC AAG AAC GCT GCC
                                27
 AAC TAC GTC GGT GAC AAG GTC CAG G GTAGGTTTCCTCC AGCTCTCGCC
                               82
TCCAGCACCC  GAGGCACATC TCGGGCATCT TCACAAC AGCAGACACTGAC
                           139
ATCTCATTCT CACAG GC  GCT ACC GCC ACT GCT TCC AAG GAG GCC AAC
                              187
AAG GAC GTT GCC AAG GAC  TCC AAC CAG GGC GTC GGC ACT CG
                                       240
GTAAGCTCCA TCACTTTTCC ACTCTCACAG  CCATCATCAG ACACTAACAT
                                           294
TCATCTTCCTCTCAG T CTC AAC GCT GCC GGT GAT  GCC ATC TCC GAC
                                                   342
AAG GTC TCC GAG AAC AAG CAC GAC GCT AAG GCC GAG  GCC CAC AAG
                                                        395
CAG GGT GCT ACC CAC TAA GCGACT TTACCAACAG TCGTTTTCCA

TTTCCTTTTT ATCAGTCATG ACTTGATGAT AATGGCCGGC TAAGGAGTTC
```

```
     455
GCCAAGGGCT   TCTCTATGAC ATACTTGGCT TGGAATTTCG AAGGGCAGCT

515
TTAGCATTAC ACCAGAACCG   ATACCCCTAT TACATAGGCA TGGACACTGG

575
TCCGTTCTAG CTAGGAATTG ACCCGGCTCT   CTGCCAATTA ATACCTTCAC

635
ATCTGTTTTT TTCCTCTTTG TTTTTGTGAC ATTGACATTG   CCTTTCTGAC

695
ATTGCTGTGT GCTTTGCAAC TTTGATCTTT ATAATTCTAC TTTGGCATTT

GGGGGGATTA TAAATGAGCC ATCGTCTTCA CGACTTGACT TAATGTAATA

755
GCAGTGACAC   GAAAAGTTCG GCAAACATCA ACAACCCCAA ATGTCTTGCA

815
TGAGACAGTG TTGATCCAGA   CCCTCAATAA GCTGAACGAC ACTAGCAGGG

875
GCTGTGCACG GGCCACAAAG ATCAGCCCTC   GCGATGAACT TCGCGTCCT

935
CAAGATTTCG GAGGCCACTT CGTTGAGGCC CAGCATC     TCGT AACT

962
GGCAAGAAAC ACAGCTG ;
``` b) a DNA sequence of eukaryotic or prokaryotic origin inserted into said glucose-repressible gene region and replacing all, or a portion thereof, of the gene grg-1 which is from about nucleotide 1 to about nucleotide 369, wherein the transcription of said chimeric gene into m-RNA is regulatable; and c) a regulatory region which regulates the transcription of said chimeric gene, wherein said regulatory region comprises all, or a portion thereof, of the nucleotide sequence from about nucleotide −1 to about nucleotide −926 of said glucose-repressible gene region.

2. The chimeric gene of claim 1, wherein said regulatory region further comprises an additional upstream nucleotide sequence which increases the level of transcription to m-RNA, said upstream nucleotide sequence consists essentially of the following nucleotide sequence:

```
1
CTCGAGTTGC ACGTGCCCTT TCTTGCACAC GAGTTCGCCT GTTAAAACAT

CCCGGCGTCA AGGGCAGTCG CTGTCCGTTG GTCTACCCGT TCATTGGAAT
101
TTCTCTTGGC GGCCTTGGTG AGGATGGCTC GATGGGTTAT ACGGAGTTCG

GTTGAACGTG GCACTGATGC GAGCTGCTTC TGTTACACCC GACGAAGTCG
201
GTCTTCCTCC CAACATCCGT CCTGAACCTG CTTCACCCAC GAAACCGAGA

TGATGCCACT GCACGATCTG ACCACCCTCC CAAATTCTGT TGAGTCTTGA
301
CTCTCAACAA GTGCCCGGGC CTGTTGCCTT TCACCCACGT CAAGAATGCC

AACGAGCAGA ACGCCCTGTG CTCCTTCCAT CTCATAGATC GTGATATTTG
401
ATTTTGCAAA  GGTAAGAA CTTGACGGCA CCTGTCAGCT GATGAAGAAA

AGGCAAGTTC CAACCGGGCG CAATCATCGC TAAGCTCAAG AAGCTAATGG
501
TTCCTGCCGC TCATATCTGT TGATGGATAT TGGTACATCG ATAGTTTTGC

ACCTCTGCAT GGATATAAAG GGTTAGCTTG GTACGATGAG CCTACATAAA
601
ATATGGAGTA GACAGATGAC AGGAGAGCCA TTTCCTGTGC CAAAACCAAG

CTTCTTTGCC ACTCGCAGGA ACCGAGCTAA TATTTACACT ACACAATGCA
701
GAGGCGCCCA AGCTGCAAGT CATCGCCGAT TCGTTTCATC TCGAGCCAGG

CTCGCAGGCA CAAAGCACGC TGGGAAGAGG AGCAACGTTC ACTGGGCGGG
801
CCTCGAACCG TCGGTAGTTC CTCTTGCCAA TGGGATTCGC TGCCCGTGTT

TGGCGAGCTT GGTCTCTAGT GCAGAGCAAC CCCTCATTTG GGGAATCCAG
901
CGAGCAATCT GTTGCACGTT GGGAAAGGCA GGAGCGCAAT CTTCCTATCA

GCTGCTCACA CTCGTCAGTG CATCATCGAA GAGCCGAATT GCCATGGAGA
1001
AACAGGATGG GAATCTGGCA ATCCGAGGAA TCTCGCCACT GGCTCCAACA

GATCATTCAA CCGAGGCAGG AGGATCTACC AATGCGAGGC GCCTTTCGTA
1101
CGTTCATTTA CAAAATTGAA CCAAGATCAA GATGACCGTG TTCTCGGTTT

GATACTATGG AGCCCACGGC TGTTCAAGTC CTGTGTGAAT GCAAGTCGGC
1201
CGCAGCGGCT CCTCCCCAGA TTTCAGATTG TAGTATGTAC CTAGCAGTGC

GGGCATAAGT AGCTAGCTGC ACATCAATAG TGCGGGCTCA GCTAATGGGA
1301
ATCGTTCTTT GACGGCCAGC CCTGCCATGC GTCACTGGCC GGGATAATGG

CCCATGATGC CTCTTTCCAT TTCCGGAAGT TTGTGTACTT TCGCCTAAAC
1401
ACGAGATGTG ATTCTCAGGC AACGACGCGG AAGGAGAGAG CCCAAAGTCG

GGCGCGTCTT GTTC .
```

3. The chimeric gene of claim 1, wherein said gene is capable of being cloned into a vector.

4. The chimeric gene of claim 3, wherein said vector comprises a plasmid containing a gene which can be utilized in the selection of transformants.

5. The chimeric gene of claim 4, wherein said vector is introduced into a eukaryotic microorganism.

6. The chimeric gene of claim 5, wherein said eukaryotic organism is a filamentous fungus.

7. The chimeric gene of claim 6, wherein said filamentous fungus is of the Neurospora genera.

8. The chimeric gene of claim 7, wherein said filamentous fungus is *Neurospora crassa*.

9. A recombinant plasmid containing the chimeric gene of claim 1 or 2.

10. A eukaryotic microorganism containing the plasmid of claim 4 or 9.

11. A method for efficient production of a recombinant protein comprising:

a) introducing a vector containing the chimeric gene of claim 1 or 2 into a eukaryotic microorganism;

b) growing a culture of the microorganism of a) in an appropriate glucose containing medium, wherein the glucose is fermented during the exponential growth phase;

c) depleting the glucose in the culture medium during the growth phase such that her grg-1 regulatory region of said chimeric gene turns on the production of m-RNA encoding the recombinant protein thereby synthesizing said protein; and d) purifying the recombinant protein from the culture medium.

12. The method of claim 11, wherein said vector is a plasmid containing a gene which can be utilized in the selection of transformants.

13. The method of claim 12, wherein said eukaryotic microorganism is a filamentous fungus of the Neurospora genera.

* * * * *